(12) United States Patent
Lander et al.

(10) Patent No.: US 6,867,052 B2
(45) Date of Patent: Mar. 15, 2005

(54) BIOLOGICAL MATERIAL DETECTING ARTICLES OF MANUFACTURE

(75) Inventors: Terri Lander, Juno Beach, FL (US); William T. Bodenhamer, Jupiter, FL (US)

(73) Assignee: Toxin Alert, Inc., Ontario (CA)

( * ) Notice: Subject to any disclaimer, the term of this patent is extended or adjusted under 35 U.S.C. 154(b) by 185 days.

(21) Appl. No.: 10/002,402

(22) Filed: Oct. 25, 2001

(65) Prior Publication Data

US 2003/0211635 A1 Nov. 13, 2003

Related U.S. Application Data

(63) Continuation-in-part of application No. 09/724,438, filed on Nov. 28, 2000, now Pat. No. 6,692,973, which is a continuation-in-part of application No. 09/550,777, filed on Apr. 17, 2000, now Pat. No. 6,376,204, and a continuation-in-part of application No. 09/550,779, filed on Apr. 17, 2000, now Pat. No. 6,379,908, which is a continuation-in-part of application No. 09/218,827, filed on Dec. 22, 1998, now Pat. No. 6,051,388.

(51) Int. Cl.[7] ............................................. G01N 33/543
(52) U.S. Cl. ........................ 436/518; 422/50; 422/55; 422/56; 422/57; 422/58; 422/61; 435/6; 435/7.1; 435/7.2; 435/287.1; 435/287.2; 435/287.7; 435/287.8; 435/287.9; 435/288.7; 435/805; 435/810; 436/164; 436/169; 436/170; 436/63; 436/66; 436/524; 436/528; 436/531; 436/805; 436/810; 436/815; 436/827
(58) Field of Search .............................. 422/50, 55, 56, 422/57, 58, 61; 435/6, 7.1, 7.2, 287.1, 287.2, 287.7, 287.8, 287.9, 288.7, 805, 810; 436/164, 169, 170, 68, 66, 518, 524, 528, 531, 805, 810, 815, 827

(56) References Cited

U.S. PATENT DOCUMENTS

| 3,672,351 A | * | 6/1972 | Ubersax et al. ................ 422/50 |
| 4,473,079 A | * | 9/1984 | Jasper et al. ................... 422/56 |
| 4,870,005 A | | 9/1989 | Akiyoshi et al. |
| 4,966,856 A | | 10/1990 | Ito et al. |
| 5,614,375 A | | 3/1997 | Citri |
| 5,650,329 A | * | 7/1997 | Warner ........................ 436/101 |
| 5,756,291 A | | 5/1998 | Griffin et al. |
| 5,776,672 A | | 7/1998 | Hashimoto et al. |
| 5,869,341 A | | 2/1999 | Woodaman |
| 5,898,373 A | | 4/1999 | Murad et al. |
| 5,976,881 A | * | 11/1999 | Klingner ....................... 422/58 |
| 6,020,047 A | | 2/2000 | Everhart |
| 6,051,388 A | | 4/2000 | Bodenhamer |
| 2002/0045200 A1 | | 4/2002 | Bodenhamer |

FOREIGN PATENT DOCUMENTS

| WO | WO00/37934 | 6/2000 |
| WO | WO01/79840 | 10/2001 |
| WO | WO01/79850 | 10/2001 |

OTHER PUBLICATIONS

Berkeley Lab RESEARCH NEWS, Dec. 10, 1996, New Sensor Provides First Instant Test for Toxic *E. Coli* Organism by: Jeffrey Kahn.

Wang et al., "An Immunie–capturing and concentrating procedure for *Escherichici coli*", Food Microbiology (1998), vol. 15., pp. 559–565.

* cited by examiner

*Primary Examiner*—Christopher L. Chin
(74) *Attorney, Agent, or Firm*—McHale & Slavin, P.A.

(57) ABSTRACT

The present invention relates to articles of manufacture inclusive of or in combination with a biological assay material, formed from a material capable of detecting and identifying the presence of one or more particular toxic substances, wherein said toxic substances may comprise a multiplicity of biological materials.

15 Claims, No Drawings

BIOLOGICAL MATERIAL DETECTING ARTICLES OF MANUFACTURE

CROSS-REFERENCE TO RELATED APPLICATIONS

This application is a continuation-in-part of U.S. Ser. No. 09/724,438, filed Nov. 28, 2000 now U.S. Pat. No. 6,692,973, which is a continuation-in-part of copending applications U.S. Ser. No. 09/550,777, filed on Apr. 17, 2000, now U.S. Pat. No. 6,376,204; and U.S. Ser. No. 09/550,779, filed on Apr. 17, 2000, now U.S. Pat. No. 6,379,908; respectively; which are continuations-in-part of U.S. Ser. No. 09/218,827, filed Dec. 22, 1998, now U.S. Pat. No. 6,051,388; all of the contents of which are herein incorporated by reference.

FIELD OF THE INVENTION

This invention relates to articles of manufacture comprising a biological assay material for detecting the presence of a particular toxic substance; particularly to articles of manufacture comprising active areas which are constructed and arranged for the diagnostic detection and identification of pathological agents; and most particularly to articles of manufacture particularly designed for detecting and identifying one or a plurality of materials which are biologically hazardous.

BACKGROUND OF THE INVENTION

Although considerable effort and expense have been put forth in an effort to control food and/or airborne pathogenic microorganisms, there nevertheless exist significant safety problems in the supply of packaged food, in the certification of sterility for medically useful components, e.g. surgical tools, internal examination devices, e.g. endoscopes, and the like, and in dealing with the use of a variety of biological materials as weapons of mass destruction.

For example, numerous outbreaks of food poisoning brought about by foodstuffs contaminated with strains of the E. coli, Campylobacter, Listeria, Cyclospora and Salmonella microorganisms have caused illness and even death, not to mention a tremendous loss of revenue for food producers. These and other microorganisms can inadvertently taint food, even when reasonably careful food handling procedures are followed. The possibility of accidental contamination, for example by temperature abuse, in and of itself, is enough to warrant incorporation of safe and effective biological material diagnosis and detection procedures. Further complicating the situation is the very real possibility that a terrorist organization might target either the food or water supply of a municipality or even a nation itself, by attempting to include a pathogenic microorganism or toxic contaminant capable of causing widespread illness or even death. If, by accident or design, the food supply of a particular population were to be contaminated, it is not only imperative that the population be alerted to the contamination, but it is further necessary that the particular contaminant be quickly and precisely pinpointed so that appropriate countermeasures may be taken.

With respect to medical or dental procedures, there exists a very real possibility for transmission of disease due to ineffective sterilization techniques or careless handling of medical implements, which can often lead to contamination of the sterile field. Although these devices are generally wrapped after sterilization, it is impossible to verify the efficacy of the sterilizing process or determine if subsequent contamination has occurred prior to use.

Additional attention is directed toward the use of potential agents of bioterrorism, e.g. various bacteria, viruses, or toxins, which can be of microbial, plant, or animal origin, also represent a credible threat to the general population, since they can be incorporated within biological weapon systems of mass destruction. The most common agents of concern include Bacillus anthracis (anthrax), Yersinia pestis (plague), Variola major virus (smallpox), and botulinum toxin. Additional potential agents include: brucella sp.; Venezuelan equine encephalitis (VEE) virus and other viral encephalidities; Vibrio cholerae (cholera); and, staphylococcal enterotoxin B (SEB).

The technology required to creates weapons of mass destruction from biological agents is readily available to the civilian population in the form of texts and information available via the Internet. Modestly financed organizations of relatively small size and rather basic training in biology and engineering could easily develop an effective biological weapons capability.

Individual agents and toxins useful as biological weapons generally share the following features: (1) capability of being dispersed as aerosols and remain suspended for hours; (2) aerosols are deliverable by simple technology readily available in industry, e.g., agricultural crop dusters, backpack sprayers, purse-size perfume atomizers, and the like; and, (3) aerosols are capable of producing significant, if not fatal, illness in humans when inhaled.

In contrast to screening methods used to detect traditional explosive devices (e.g., x-ray and trained canines), there are essentially no routine methods or technology in place to detect a biological weapon. Additionally, variously known laboratory techniques for detecting biological agents require extensive time for development and testing of sample cultures in order to confirm a diagnosis.

Lastly, it is generally accepted that it is impossible to know either the timing for release of a biological agent or the methodology of its dispersal, e.g. aerosol, powder, via the mails, through HVAC systems, or the like.

Thus, it is imperative that articles of manufacture be developed which provide an unambiguous warning to the untrained general population, that they have come in contact with a biological weapon.

DESCRIPTION OF THE PRIOR ART

U.S. Pat. No. 6,051,388 discloses bioassay materials which may take the form of packaging materials for food or other products and which are useful for detecting toxic substances The biological assay therein disclosed broadly encompasses a base layer which is a flexible polyolefin film having a surface which has undergone a treatment step effective to enhance the film's ability to immobilize a ligand which has been applied thereto and a biologically active ligand which is immobilized to the film subsequent to which a protectant layer in the form of a gel coat or liquid film is applied. This patent requires separate deposition of the active ligand followed by application of the protectant layer.

U.S. Pat. No. 4,966,856 discloses an analytical element having a layer for antibody/antigen binding but fails to teach or suggest a flexible polyolefin matrix.

U.S. Pat. No. 4,870,005 teaches a multi-layer analysis element including a membrane filter to which an antigen or antibody is immobilized. The concept of forming a flexible analysis element having immobilized biological agents bound thereto is neither suggested nor disclosed.

U.S. Pat. No. 6,020,047 discloses a polymer film coated with a metal alloy and containing a self-assembling monolayer printed on the polymer film.

U.S. Pat. No. 5,898,373 discloses a method for monitoring a site for the presence of future toxic agents. The patent places sticky polymeric particles upon a site to be remotely monitored for toxins over a future time period. Upon contact with a toxic agent, the particles react to produce or reflect a particular spectral signature which may be verified via an airborne vehicle using a laser transmitter or the like investigative tool.

U.S. Pat. No. 5,614,375 teaches a method and a test kit for rapidly detecting biotoxic contaminants. Activated spores, devoid of enzymatic activity, are germinated and enzymatic activity is determined in the presence of a material which is catalytically convertible to a product by the enzymatic activity. Conversion of the material is determined as a means of verifying the presence of the toxic material.

The Berkeley Lab Research News of Dec. 10, 1996, in an article entitle "New Sensor Provides First Instant Test for Toxic *E. coli* Organism" reports on the work of Stevens and Cheng to develop sensors capable of detecting *E. coli* strain 0157:H7. A color change from blue to red instantaneously signals the presence of the virulent *E. coli* 0157:H7 microorganism. Prior art required test sampling and a 24 hour culture period in order to determine the presence of the *E. coli* microorganism, requiring the use of a variety of diagnostic tools including dyes and microscopes. An alternative technique, involving the use of polymerase chain reaction technology, multiplies the amount of DNA present in a sample until it reaches a detectable level. This test requires several hours before results can be obtained. The Berkeley sensor is inexpensive and may be placed on a variety of materials such as plastic, paper, or glass, e.g. within a bottle cap or container lid. Multiple copies of a single molecule are fabricated into a thin film which has a two part composite structure. The surface binds the biological material while the backbone underlying the surface is the color-changing signaling system.

The Berkeley researchers do not teach the concept of incorporating any means for self-detection within food packaging, nor do they contemplate the inclusion of multiple means capable of both detecting and identifying the source of pathogenic contamination to a technically untrained end user, e.g. the food purchaser or consumer.

Wang et al, in an article entitled "An immune-capturing and concentrating procedure for *Escherichia coli* 0157:H7 and its detection by epifluorescence microscopy" published in Food Microbiology, 1998, Vol. 15 discloses the capture of *E. coli* on a polyvinylchloride sheet coated with polyclonal anti-*E. coli* 0157:H7 antibody and stained with fluorescein-labeled anti-*E. coli* 0157:H7. After being scraped from the PVC surface, the cells were subjected to epifluorescence microscopy for determining presence and concentration. The reference fails to teach or suggest the concept of incorporating any means for self-detection within food packaging, nor does it contemplate the inclusion of multiple means capable of both detecting and identifying the source of pathogenic contamination to a technically untrained end user, e.g. the food purchaser or consumer, and especially fails to disclose such detection without the use of specialized detection techniques and equipment.

U.S. Pat. No. 5,776,672 discloses a single stranded nucleic acid probe having a base sequence complementary to the gene to be detected which is immobilized onto the surface of an optical fiber and then reacted with the gene sample denatured to a single stranded form. The nucleic acid probe, hybridized with the gene is detected by electrochemical or optical detection methodology. In contrast to the instantly disclosed invention, this reference does not suggest the immobilization of the probe onto a flexible polyvinylchloride or polyolefin film, nor does it suggest the utilization of gelcoats having varying porosities to act as a control or limiting agent with respect to the migration of antibodies or microbial material through the bioassay test material, or to serve as a medium for enhancement of the growth of the microbial material.

U.S. Pat. No. 5,756,291 discloses a method of identifying oligomer sequences. The method generates aptamers which are capable of binding to serum factors and all surface molecules. Complexation of the target molecules with a mixture of nucleotides occurs under conditions wherein a complex is formed with the specific binding sequences but not with the other members of the oligonucleotide mixture. The reference fails to suggest the immobilization of the aptamers upon a flexible polyvinylchloride or polyolefin base material, nor does it suggest the use of a protective gelcoat layer which acts as a means to selectively control the migration of antibodies and antigens, or to serve as a medium for enhancement of the growth of microbial material.

The prior art fails to teach an article of manufacture which is readily providable to the populous, and which can provide an unskilled person with a visual signal capable of alerting said individual to the presence of a toxic agent while simultaneously identifying the toxic agent with which the individual has come into contact.

SUMMARY OF THE INVENTION

The present invention relates to articles of manufacture inclusive of or in combination with a biological assay material, wherein "in combination" may be defined as integral therewith, or appended thereto or thereon. The articles of the instant invention are formed a material capable of detecting and identifying a multiplicity of biological materials.

In one embodiment, the article of manufacture, which is contemplated as including various articles of clothing (non-limiting examples of which are gloves, lab-coats, booties, hats, face masks, and the like) labels, envelopes, bags or pouches, self-adherent patches, and the like; are formed so as to provide an integral biological material identification system. By "integral" it is meant that the biological material detection system may constitute the material of construction of the biological assay material, may be applied directly to the article of manufacture, or alternatively, said article may be constructed and arranged to accept a portion of said biological material detection system thereon, in an amount effective to provide the desired indication of contamination. In such an embodiment, the biological material detection system is designed to be easily replaced so that the base article is instantly reusable upon application of a new or different biological assay material. Thus, using gloves as an illustrative embodiment, such gloves could be formed for extended use, while the biological assay material could be easily rejuvenated or changed, so as to facilitate maintenance of the diagnostic efficacy of the gloves or alternatively to enable instantaneous customization of the gloves for a particular detection utility. Given the varying means by which the biological material detecting system of the instant invention can be included in combination with various articles of manufacture, the widespread inclusion of the biological material detecting system in a variety of manufactured articles will be both efficient and economical.

In one embodiment of the invention the biological material detecting system prints a pattern containing several of the biologically active agents, e.g. antibodies or aptamers onto a flexible material which is usually a type of polymeric film, preferably a polyvinyl chloride or polyolefin film.

Each biological agent, for example an antibody, can be tailored so as to be specific to a particular biological material and may be printed upon the substrate in a distinctive icon shape. The detection system may contain any number of biological agents, or a variety of epitopes thereof, capable of detecting a variety of common toxic microbes, less common microbes useful as biological weapons, or combinations thereof. Although any number of microbes may be identified via the inventive concept taught herein, for the purpose of this description, the microbes of interest will be directed toward Anthrax, Smallpox, Plague and Botulism.

The biological material detecting system will not merely detect the presence of biological materials, it will also identify the particular biological materials located in a packaged product. This unique feature allows for the immediate identification of each particular biological material present since the antibodies are specific to a detector having a definitive icon shape or other identifying characteristic. As an illustrative, but non-limiting embodiment of the invention, a plurality of icons, each relevant to a particular biohazard, e.g. Anthrax, Smallpox, Plague, Botulism and the like, can be applied to the substrate via various printing techniques, as are set forth in U.S. Pat. No. 6,051,388 and related applications, all of whose contents have been herein incorporated by reference. Upon contact with one or more of the biohazards, the icons will change from their original visual image to an image which is indicative of said contact, thereby alerting the viewer of a dangerous situation, while simultaneously identifying the biohazard.

The ability to detect and identify the particular biological material immediately is of immeasurable value to health officials and governmental agencies. The ability to immediately identify a toxic material will lead to greatly reduced response times to health threats that might be caused by the biological material and will also enhance the ability for authorities to locate the source of the problem.

In an alternative embodiment, the biological material detection system may be formed upon any suitable substrate e.g. any flexible transparent polymer film, and subsequently be combined with a secondary material, illustrated, but not limited to, a paper or cloth backing, which may further contain means for adherence to yet an additional article. In such manner, an article of manufacture useful for producing an unlimited variety of end-products is contemplated by the invention.

As a means of providing enhanced sensitization, a scavenger antibody, which is a biologically active ligand characterized as having a higher affinity for the particular toxic substance than the capture antibody, may be included. The scavenger antibody is provided, e.g. by mixing said scavenger body with the combined capture antibody/water gloss overprint varnish, in a sufficient amount to bind with the particular toxic substance up to and including a specific threshold concentration. In this manner, the capture antibody will be prevented from binding with a detector antibody until the concentration of the particular biological material surpasses the specific threshold concentration. In this manner, the biological material detecting system visually reports only those instances where concentration levels are deemed harmful by health regulatory bodies.

The biological material detecting system of the present invention exhibits an active shelf life in excess of 1 year under normal operating conditions. This enhances the use of a biological material detection system on products which are intended to be stored for long periods of time, e.g. military rations or medical supplies, which might come into contact with biological hazards. These products are stored so as to be ready for immediate use in some time of emergency, therefore it is extremely beneficial to be able to readily determine their safety at the time of use.

The articles of manufacture which incorporate the biological material detecting system, as set forth in the instant invention, represent an entirely new device for alerting the general population to the presence of toxic materials in the environment. They provide the layman with a simple device, which is easily substituted for non-biologically sensitive devices, which will readily alert users to the presence of certain biologically hazardous materials present in food stuffs, mail, newspapers, or the like.

The system is designed so that the presence of a biological material is indicated to the user in a distinct, unmistakable manner which is easily visible to the naked eye.

An important feature of the biological material detection system is the plurality of testing sites which it provides. In the past, the use of single location or in situ detectors have left a majority of the area around and upon a particular location exposed to undetected microbes. This greatly increased the chance that a hazardous, spoiled or tainted product might be inadvertently passed along or consumed before the toxic agent had spread to the location of the in situ detector. The biological material detection system of the present invention avoids this problem by providing a plurality of individual detectors per unit area which are effective to maximize detection of any hazardous microorganisms within, upon or around the area of concern.

It is an objective of the present invention to provide an article of manufacture which comprises a biological material detecting system for protecting against, or warning of the presence of, a biologically hazardous material. Awareness of the hazardous material is accomplished by detecting and unmistakably presenting to the untrained eye visual icons on said article which signify the presence of one, or a plurality, of hazardous microorganisms.

It is another objective of the instant invention to provide an article of manufacture which integrates a bioassay material detection system, wherein an antigen detecting antibody system is immobilized within a biological activity maintaining matrix (e.g. a gelcoat layer and/or a varnish matrix) upon the surface of a flexible polymer.

It is still another objective of the instant invention to provide an article of manufacture comprising a bioassay material wherein an antigen detecting antibody system is immobilized upon the surface of a suitable substrate, e.g. a flexible member formed from a polymer film, or a composite laminated structure including said film.

It is a further objective of the invention to provide an article of manufacture inclusive of a biological material detecting system which is so similar in appearance and utilization that its use, in lieu of traditional articles of manufacture, is not apparent to the end user.

A still further objective of the present invention is to provide an article of manufacture inclusive of a biological material detecting system which is cost effective when compared to traditional packaging materials.

Yet an additional objective of the instant invention is to provide an article of manufacture inclusive of a biological material detecting system applied to a substrate.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

The particular toxic substance may be one or more members selected from the group consisting of a particular microorganism, biological materials containing the genetic characteristics of said particular microorganism, and mutations thereof. In a particular embodiment, the toxic substance is selected from the group consisting of microorganisms, nucleic acids, proteins, integral components of microorganisms and combinations thereof.

It should also be understood that the invention will function by direct measurement of microbes with certain types of antibodies, selected from the group consisting of an antibody, a single stranded nucleic acid probe, an aptamer, a lipid, a natural receptor, a lectin, a carbohydrate and a protein. The biological materials may also be measured by non-immunological methods in particular using labeled molecules, such as aptamers, which have a high affinity for the biological materials.

The invention utilizes various types of detector antibodies, e.g. those conjugated with dyes to produce a visual cue, or alternatively, photoactive compounds capable of producing a visual cue in response to a particular type of light exposure, for example a scanning system which detects luminescent properties which are visualized upon binding of the antigen and antibody. In this method of construction biological materials are measured directly with a biologically active ligand, e.g. an antibody, aptamer, nucleic acid probe or the like, which induces a conformational change to produce a visual cue.

It is also understood that specific polymers may be incorporated into the invention and that when a biological material is bound to the surface it induces a molecular change in the polymer resulting in a distinctly colored icon.

The inventor has now discovered that it is possible to form composites by attaching biologically active ligands to the surface of various substrates, e.g. flexible cellulosic materials, e.g. paperstock, flexible polymers, flexible spun or woven materials, and the like, for example polyvinyl chloride, TYVEK, various polyolefins either singly or in varying combinations, e.g. a polyolefin sheet having appropriate properties of transparency and flexibility and that the composite functions as a biological sensor or assay material. These films may be untreated polyethylene or polyvinyl chloride films which are amenable to antibody immobilization by various mechanisms, e.g. by adsorption. In a particular embodiment, the films may be first cleaned, e.g. by ultrasonication in an appropriate solvent, and subsequently dried. For example the polymer sheet may be exposed to a fifteen minute ultrasonic treatment in a solvent such as methylene chloride, acetone, distilled water, or the like. In some cases, a series of solvent treatments are performed. Subsequently the film is placed in a desiccating device and dried. Alternatively, these films may be created by first exposing the film to an electron discharge treatment at the surface thereof, then printing with a fluorescing antibody receptor. Subsequently, a drying or heating step may be utilized to treat the film to immobilize the receptor.

Additional modifications to polyolefin films may be conducted to create the presence of functional groups, for example a polyethylene sheet may be halogenated by a free radical substitution mechanism, e.g. bromination, chlorosulfonation, chlorophosphorylation or the like. Furthermore, a halodialkylammonium salt in a sulfuric acid solution may be useful as a halogenating agent when enhanced surface selectivity is desirable.

Grafting techniques are also contemplated wherein hydrogen abstraction by transient free radicals or free radical equivalents generated in the vapor or gas phase is conducted. Grafting by various alternative means such as irradiation, various means of surface modification, polyolefin oxidation, acid etching, inclusion of chemical additive compounds to the polymer formulation which have the ability to modify the surface characteristics thereof, or equivalent techniques are all contemplated by this invention.

Additionally, the formation of oxygenated surface groups such as hydroxyl, carbonyl and carboxyl groups via a flame treatment surface modification technique is contemplated.

Further, functionalization without chain scission by carbene insertion chemistry is also contemplated as a means of polymer modification.

Illustrative of the types of commercially available films which might be utilized are polyvinyl chloride films and a straight polyethylene film with electron discharge treatment marketed under the trademark SCLAIR®. The electron discharge treatment, when utilized, renders the film much more susceptible to immobilization of the antibodies on its surface. Additional films which might be utilized are Nylon 66 films, for example DARTEK®, a coextrudable adhesive film such as BYNEL® and a blend of BYNEL® with polyethylene film.

Articles of manufacture include, but are not limited to protective gloves, booties, hats, face masks, and the like garments or articles in which the artisan is desirous of including a biological material detection and identification ability.

Additional articles of manufacture contemplated by the invention include, but are not limited to containers, e.g. document handling containers, such as mailbags, bags, boxes, envelopes, and the like; various signs and/or labels which may be self-adherent to a particular surface, and badges or tags which may be applied or attached to other articles or structures. The assay material may be attached directly to a substrate of choice, or alternatively a flexible substrate which includes the biological assay utility may be included in combination with a base article, to form a composite structure.

The invention will be further illustrated by way of the following examples, any of which may be fashioned into any of the contemplated articles:

EXAMPLE 1

Detection of Antibody on the Surface of a Thin Layer Polyvinylchloride Sheet:

Rabbit polyclonal IgG was diluted to a final concentration of 2.0 $\mu$g/ml in 0.1M carbonate ($Na_2CO_3$)-bicarbonate ($NaHCO_3$) buffer, pH 9.6.

Using a 2"×3" grid, 75 $\mu$L (150 ng) was applied to a sheet of polyvinylchloride at 1" intervals.

The antibody treated polyvinylchloride sheet was dried for 1.5 hrs. at a temperature of 37° C.

The dried sheet was then washed 3 times with a phosphate buffered saline solution at a ph of 7.4.

HRP conjugated goat anti-rabbit IgG (G$\alpha$R$^{HRP}$) was diluted to a concentration of 1:7000 in 1% casein, 0.1M potassium ferricyanide $K_3Fe(CN)_6$, 0.1% phosphate glass ($Na_{15}P_{13}O_{40}$—$Na_{20}P_{18}O_{55}$), at a pH of 7.4.

A precision pipette was used to apply 125 $\mu$L of diluted GHRP to the grid backed polyvinylchloride sheet at 1" intervals coinciding with the area covered by the previously coupled R$\alpha$G.

The sheet was incubated at room temperature for 30 minutes.
The sheet was then washed 3× with phosphate buffered saline at a pH of 7.4.
125 µL of precipitating TMB enzyme substrate was added to the test areas.
The sheet was incubated at room temperature until color development was complete.
Lastly the sheet was washed 3 times with deionized water and allowed to air dry.

EXAMPLE 2
Full Sandwich Immunoassay on the Surface of a Thin Layer Polyvinylchloride Sheet Rabbit polyclonal IgG was diluted to a final concentration of 2.0 µg/ml in 0.1M carbonate ($Na_2CO_3$)-bicarbonate ($NaHCO_3$) buffer, pH 9.6.

A 13×9 cm piece of thin layered polyvinylchloride sheet was inserted into a BIO-RAD DOT-SPOT apparatus possessing 96 sample wells spaced at 1.0 cm intervals in a 12×8 well grid.

A 100 µL sample (1.0 µg) of rabbit polyclonal IgG was applied to each well 8 of column 1.

Antibody samples applied to columns 2–12 represented serial dilutions of the antibody ranging from 500 ng–0.5 ng.

The antibody treated polyvinylchloride sheet was dried overnight at 37° C.

The dried sheet was washed 3 times with phosphate buffered saline (PBS), pH 7.4.

Antigen was diluted to a final concentration of 1.0 µg/ml in tris buffered saline (TBS) with 1% casein, pH 7.4.

100 µL, representing 100 ng, of antigen, was applied to each well of the apparatus and incubated at room temperature for 1 hour.

The polyvinylchloride sheet was washed 3 times with phosphate buffered saline (PBS), pH 7.4.

Detector mouse monoclonal antibody was diluted 1:625 with TBS containing 1% casein, 0.1M potassium ferricyanide $K_3Fe(Cn)_6$, and 0.1% phosphate glass ($Na_{15}P_{13}O_{40}$—$Na_{20}P_{18}O_{55}$), pH 7.4.

100 µL of the 1:625 dilution of detector antibody solution was applied to each well of row #1.

Detector samples of 100 µL applied to rows 2–7 represented serial dilutions of the antibody ranging from 1:1,250 to 1:80,000. Dilutions of detector antibody were incubated on the polyvinylchloride sheet for 1 Hr. at room temperature.

The polyvinylchloride sheet was washed 3 times with phosphate buffered saline (PBS), pH 7.4.

100 µL of goat anti-mouse $IgG^{HRP}$ were added to each well of the DOT-SPOT apparatus and allowed to incubate for one hour at room temperature.

The polyvinylchloride sheet was washed 3 times with phosphate buffered saline (PBS), pH 7.4.

100 µL of precipitating TMB enzyme substrate was added to the test areas.

The sheet was incubated at room temperature until color development was complete.

Lastly the sheet was washed 3 times with deionized water and allowed to air dry.

EXAMPLE 3

1. Water Gloss FDA Overprint Varnish WVGOO1006 was diluted with UHF pure water to final concentrations of 1:2, 1:5, 1:10, 1:20, 1:40, and 1:80.

The varnish has the properties of being grease resistant, heat resistant to 175° F., 30 PSI, 2 sec. dwell, Krome Kote, face to paper; COF 25°–30° F., clear, glossy finish, non-scuff resistant, not imprintable, viscosity/CPS 20–25 sec, #3 Zahn at 77° F., pH 9.2–9.6.

2. A monoclonal anti-Listeria monocytogenes capture immunoglobulin (MAb 833) was added to each dilution of the varnish, including one aliquot of neat (undiluted) varnish, for a final concentration of 20 µg/mL in each sample.

3. A sheet of corona discharge treated PE was placed between two pieces of acrylic, of which the uppermost component served as a template. The template possessed 7 columns of 5 bottomless X shaped wells in which samples could be applied directly to the surface of the PE. The two acrylic components were secured by a series of clamps and bolts to prevent leakage.

4. 10 µL of the undiluted varnish, containing 200 ng of immunoglobulin, was applied to each well of column 1. The procedure was repeated sequentially for the 6 varnish dilutions, beginning with the 1:2 dilution added to each of the 5 wells of column 2.

5. Samples were allowed to air dry at room temperature for 1 hour.

6. A second horseradish peroxidase (HRP) conjugated monoclonal anti-Listeria monocytogenes antibody (MAb 832) was diluted to a 1:4000 concentration in phosphate buffered saline (PBS), pH 7.4.

7. Heat killed Listeria monocytogenes cells (antigen) were added to the HRP conjugate solution at a concentration of $10^5$ cells per mL.

8. 100 µL of the antigen/conjugate solution, representing 10,000 Listeria monocytogenes cells, was added to each well of the template and allowed to incubate for 1 hour at room temperature.

9. The template was disassembled and the sheet of PE washed briefly with UHF water to remove any excess conjugate.

10. The polyethylene sheet was placed in a 50 mL bath of TMB substrate for peroxidase (available from Vector Laboratories).

11. Color development was allowed to continue for 15 minutes prior to removing the PE sheet from the substrate bath. The reaction was stopped by rinsing the PE sheet with UHF water.

Results:

1. No color development was observed in columns 1–4.
2. Distinct color development was observed in each well of columns 5–7.
3. Color could not be removed by the application and subsequent lifting of adhesive tape.

Color development indicates that the biological activity of the capture antibody applied to the PE surface is not adversely affected by Water Gloss FDA Overprint Varnish WVG001006. Alternatively, the absence of color development in columns 1–4 (neat-1:10 dilutions) indicates that a threshold exists in the concentration of varnish applied to the polyethylene surface. Binding is thus inhibited at concentrations lower than 1:20. Furthermore, the inability to remove color from the PE surface using adhesive tape indicates that binding of the immunoglobulin to the PE surface is stable and that leaching from the PE surface over time will not occur.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and drawings/figures.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An article of manufacture capable of detecting the presence of a particular toxic substance comprising:
    a substrate located on at least a portion of said article;
    a biologically active ligand capable of recognizing an epitope of the particular toxic substance on at least a portion of said substrate; and
    a matrix for maintaining biological activity of said biologically active ligand, and having immobilized therein said biologically active ligand, said matrix positioned upon said substrate;
    wherein said ligand produces a visual cue upon recognition of said toxic substance;
    whereby the presence or absence of said particular toxic substance is confirmed.

2. The article of manufacture in accordance with claim 1 wherein:
    said substrate is flexible.

3. The article of manufacture in accordance with claim 1 wherein:
    said substrate is releasably secured to said article of manufacture.

4. The article of manufacture in accordance with claim 1 wherein:
    said substrate is permanently secured to said article of manufacture.

5. The article of manufacture in accordance with claim 1 wherein:
    said substrate is formed integral with said article of manufacture.

6. The article of manufacture in accordance with claim 1 wherein:
    said substrate is a polymer film securable to said article.

7. The article of manufacture in accordance with claim 1 wherein:
    said biologically active ligand is immobilized in a particular icon shape.

8. The article of manufacture in accordance with claim 1 wherein:
    said ligand is selected from the group consisting of an antibody, a single stranded nucleic acid probe, an aptamer, a lipid, a natural receptor, a lectin, a carbohydrate and a protein.

9. The article of manufacture in accordance with claim 1 further including:
    a scavenger antibody, which is a particular biologically active ligand characterized as having a higher affinity for the particular toxic substance than said biologically active ligand, said scavenger antibody present within said substrate in a sufficient amount to bind with the particular toxic substance until a particular threshold concentration is reached;
    whereby said biologically active ligand binds with a detector antibody when the concentration of the particular toxic substance surpasses said particular threshold concentration.

10. The article of manufacture in accordance with claim 1 wherein:
    the particular toxic substance is at least one member selected from the group consisting of at least one particular microorganism, biological materials containing the genetic characteristics of said at least one particular microorganism, nucleic acids, proteins, integral components of said at least one particular microorganism and combinations thereof.

11. The article of manufacture in accordance with claim 1 wherein:
    said ligand is a chromogenic ligand.

12. The article of manufacture in accordance with claim 1 wherein:
    said biological activity maintaining matrix is a water gloss overprint varnish.

13. The article of manufacture in accordance with claim 1 wherein:
    said biological activity maintaining matrix is a gelcoat.

14. An article of manufacture selected from the group consisting of gloves, coats, shoes, hats, face masks, labels, envelopes, bags, pouches, and self-adherent patches for detecting the presence of a particular toxic substance comprising in combination:
    a substrate constructed and arranged to be releasably securable to said article of manufacture, said substrate being located on at least a portion of said article;
    a biologically active ligand capable of recognizing an epitope of the particular toxic substance on at least a portion of said substrate; and
    a matrix for maintaining biological activity of said biologically active ligand, and having immobilized therein said biologically active ligand, said matrix positioned upon said substrate;
    wherein said ligand produces a visual cue upon recognition of said toxic substance;
    whereby the presence or absence of said particular toxic substance is confirmed.

15. An article of manufacture selected from the group consisting of gloves, coats, shoes, hats, face masks, labels, envelopes, bags, pouches, and self-adherent patches for detecting the presence of a particular toxic substance comprising in combination:
    a biologically active ligand located on at least a portion of said article of manufacture, said ligand being capable of recognizing an epitope of the particular toxic substance; and
    a matrix for maintaining biological activity of said biologically active ligand, and having immobilized therein said biologically active ligand, said matrix positioned upon said substrate;
    wherein said ligand produces a visual cue upon recognition of said toxic substance;
    whereby the presence or absence of said particular toxic substance is confirmed.

* * * * *